(12) United States Patent
Haws et al.

(10) Patent No.: US 9,041,566 B2
(45) Date of Patent: May 26, 2015

(54) LOSSLESS COMPRESSION OF THE ENUMERATION SPACE OF FOUNDER LINE CROSSES

(71) Applicant: International Business Machines Corporation, Armonk, NY (US)

(72) Inventors: David C. Haws, New York, NY (US); Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 84 days.

(21) Appl. No.: 14/014,635

(22) Filed: Aug. 30, 2013

(65) Prior Publication Data

US 2015/0061903 A1    Mar. 5, 2015

(51) Int. Cl.
*H03M 7/00* (2006.01)
*H03M 7/40* (2006.01)

(52) U.S. Cl.
CPC .................................. *H03M 7/4006* (2013.01)

(58) Field of Classification Search
CPC ... H03M 7/40; H03M 7/4006; H03M 7/3084; G06N 3/086; G06N 3/12; G06N 3/00; G05B 13/0265; G06F 1/30; G06F 1/28; G06F 1/26; G06G 7/00; G06E 1/00; G06E 3/00
USPC ........................ 341/65, 67, 78, 79; 706/13–44
See application file for complete search history.

(56) References Cited

U.S. PATENT DOCUMENTS

| | | | | |
|---|---|---|---|---|
| 5,343,554 A | * | 8/1994 | Koza et al. | 706/13 |
| 5,651,099 A | * | 7/1997 | Konsella | 706/13 |
| 5,835,901 A | * | 11/1998 | Duvoisin et al. | 706/19 |
| 5,870,729 A | * | 2/1999 | Yoda | 706/26 |
| 5,974,404 A | * | 10/1999 | Moed et al. | 706/25 |
| 6,038,338 A | * | 3/2000 | Nguyen | 382/159 |
| 6,449,603 B1 | * | 9/2002 | Hunter | 706/15 |
| 6,633,244 B2 | | 10/2003 | Avery et al. | |
| 7,809,539 B2 | * | 10/2010 | Brocklebank et al. | 703/11 |

(Continued)

OTHER PUBLICATIONS

Servin, B., et al., "Toward a theory of marker-assisted gene pyramiding," Genetics, vol. 168, No. 1, Jun. 2004, pp. 513-523. Copyright 2004 by the Genetics Society of America. DOI:10.1534/genetics. 103.023358.

(Continued)

*Primary Examiner* — Linh Nguyen
(74) *Attorney, Agent, or Firm* — Fleit Gibbons Gutman Bongini & Bianco PL; Thomas Grzesik

(57) ABSTRACT

Various embodiments provide lossless compression of an enumeration space for genetic founder lines. In one embodiment, an input comprising a set of genetic founder lines and a maximum number of generations G is obtained. A set of genetic crossing templates of a height h is generated. A determination is made if at least a first genetic crossing template in the set of genetic crossing templates is redundant with respect to a second genetic crossing template in the set of genetic crossing templates. Based on the at least first genetic crossing template being redundant is redundant with respect to the second genetic crossing template, the at least first genetic crossing template is removed from the set of genetic crossing templates. This process of removing the at least first genetic crossing template from the set of genetic crossing templates the redundant creates an updated set of genetic crossing templates.

7 Claims, 7 Drawing Sheets

(56) References Cited

U.S. PATENT DOCUMENTS

| | | |
|---|---|---|
| 8,214,153 B1* | 7/2012 | Fox et al. .................. 702/19 |
| 2001/0037346 A1* | 11/2001 | Johnson .................. 707/513 |
| 2003/0004904 A1* | 1/2003 | Kirshenbaum ............ 706/13 |
| 2004/0143559 A1* | 7/2004 | Ayala ....................... 706/13 |
| 2009/0271342 A1* | 10/2009 | Eder .......................... 706/20 |
| 2011/0196872 A1 | 8/2011 | Sims et al. |
| 2012/0131029 A1 | 5/2012 | Laine |
| 2012/0330567 A1 | 12/2012 | Bauer et al. |

OTHER PUBLICATIONS

Ishii, T., et al., "Optimization of the marker-based procedures for pyramiding genes from multiple donor lines: I. Schedule of crossing between the donor lines," Crop Science, vol. 47, No. 2, Mar.-Apr. 2007, pp. 537-546.

Canzar, S., et al., "A mathematical programming approach to marker-assisted gene pyramiding," Algorithms in Bioinformatics, Springer Berlin Heidelberg, Jan. 2011, pp. 26-38.

Xu, P., et al., "An optimization approach to gene stacking," European Journal of Operational Research, vol. 214, No. 1, Oct. 2011, pp. 168-178.

Chen, X., et al., "A Compression Algorithm for DNA Sequences and Its Applications in Genome Comparison," Genome informatics, 1999, vol. 10, pp. 51-61.

Kuruppu et al., "Iterative dictionary construction for compression of large DNA data sets," IEEE/ACM Transactions on Computational Biology and Bioinformatics (TCBB), vol. 9, No. 1, Jan.-Feb. 2012, pp. 137-149.

* cited by examiner

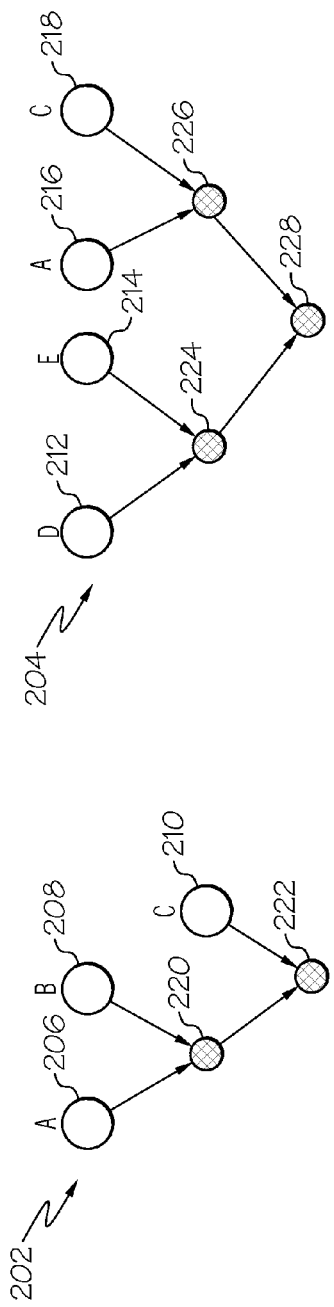
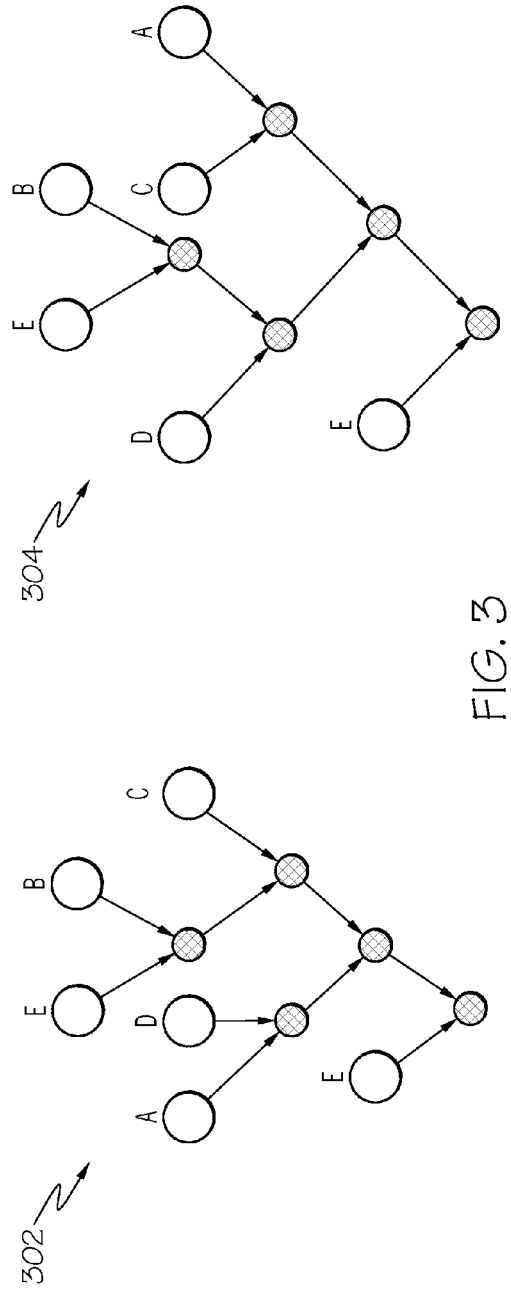
FIG. 2
FIG. 3

US 9,041,566 B2

LOSSLESS COMPRESSION OF THE ENUMERATION SPACE OF FOUNDER LINE CROSSES

BACKGROUND

The present invention generally relates to the field of computational biology, and more particularly relates to compressing the enumeration space of founder line crosses.

Identifying all possible variability that can be obtained by crossing founder lines for a given number of generations is an important task for breeders. However, redundancies usually occur during the enumeration process where two unique crossing schemes produce the same genetic variability. The computation of these redundancies waste resources and result in an inefficient enumeration process.

BRIEF SUMMARY

In one embodiment, a computer implemented method for providing lossless compression of an enumeration space for genetic founder lines is disclosed. The computer implemented method comprises obtaining an input comprising a set of genetic founder lines and a maximum number of generations G. Then, the following is iteratively performed for h=0, 1, G. A set of genetic crossing templates of a height h is generated. Each the set of genetic crossing templates represents a binary tree. The binary tree comprises h levels representing a given generation. Each of the h levels comprising a set of nodes wherein when h>0 one or more of the h levels of the binary tree correspond to at least one cross between at least one pair of nodes in the set of nodes. Each of the set of genetic crossing templates comprises an array of h entries. A position of an entry within the array corresponds to a level in the binary tree represented by the genetic crossing template. Each of the h entries in the array comprises a value indicating a number of leaf nodes in the set of nodes for the level in the binary tree. A determination is made if at least a first genetic crossing template in the set of genetic crossing templates is redundant with respect to a second genetic crossing template in the set of genetic crossing templates. Based on the at least first genetic crossing template being redundant is redundant with respect to the second genetic crossing template, the at least first genetic crossing template is removed from the set of genetic crossing templates. This process of removing the at least first genetic crossing template from the set of genetic crossing templates the redundant creates an updated set of genetic crossing templates.

In another embodiment, an information processing system for providing lossless compression of an enumeration space for genetic founder lines is disclosed. The information processing system includes a memory and a processor communicatively coupled to the memory. A genetic crossing module is communicatively coupled to the memory and the processor. The genetic crossing module is configured to perform a method. The method includes obtaining an input comprising a set of genetic founder lines and a maximum number of generations G. Then, the following is iteratively performed for h=0, 1, G. A set of genetic crossing templates of a height h is generated. Each the set of genetic crossing templates represents a binary tree. The binary tree comprises h levels representing a given generation. Each of the h levels comprising a set of nodes wherein when h>0 one or more of the h levels of the binary tree correspond to at least one cross between at least one pair of nodes in the set of nodes. Each of the set of genetic crossing templates comprises an array of h entries. A position of an entry within the array corresponds to a level in the binary tree represented by the genetic crossing template. Each of the h entries in the array comprises a value indicating a number of leaf nodes in the set of nodes for the level in the binary tree. A determination is made if at least a first genetic crossing template in the set of genetic crossing templates is redundant with respect to a second genetic crossing template in the set of genetic crossing templates. Based on the at least first genetic crossing template being redundant is redundant with respect to the second genetic crossing template, the at least first genetic crossing template is removed from the set of genetic crossing templates. This process of removing the at least first genetic crossing template from the set of genetic crossing templates the redundant creates an updated set of genetic crossing templates.

In a further embodiment, a non-transitory computer program product for providing lossless compression of an enumeration space for genetic founder lines is disclosed. The computer program product includes a storage medium readable by a processing circuit and storing instructions for execution by the processing circuit for performing a method. The method includes obtaining an input comprising a set of genetic founder lines and a maximum number of generations G. Then, the following is iteratively performed for h=0, 1, G. A set of genetic crossing templates of a height h is generated. Each the set of genetic crossing templates represents a binary tree. The binary tree comprises h levels representing a given generation. Each of the h levels comprising a set of nodes wherein when h>0 one or more of the h levels of the binary tree correspond to at least one cross between at least one pair of nodes in the set of nodes. Each of the set of genetic crossing templates comprises an array of h entries. A position of an entry within the array corresponds to a level in the binary tree represented by the genetic crossing template. Each of the h entries in the array comprises a value indicating a number of leaf nodes in the set of nodes for the level in the binary tree. A determination is made if at least a first genetic crossing template in the set of genetic crossing templates is redundant with respect to a second genetic crossing template in the set of genetic crossing templates. Based on the at least first genetic crossing template being redundant is redundant with respect to the second genetic crossing template, the at least first genetic crossing template is removed from the set of genetic crossing templates. This process of removing the at least first genetic crossing template from the set of genetic crossing templates the redundant creates an updated set of genetic crossing templates.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 2 illustrates one example of a binary tree representing a set of genetic crosses according to one embodiment of the invention;

FIG. 2 illustrates another example of a binary tree representing another set of genetic crosses according to one embodiment of the invention;

DETAILED DESCRIPTION

Operating Environment

Figure 1:
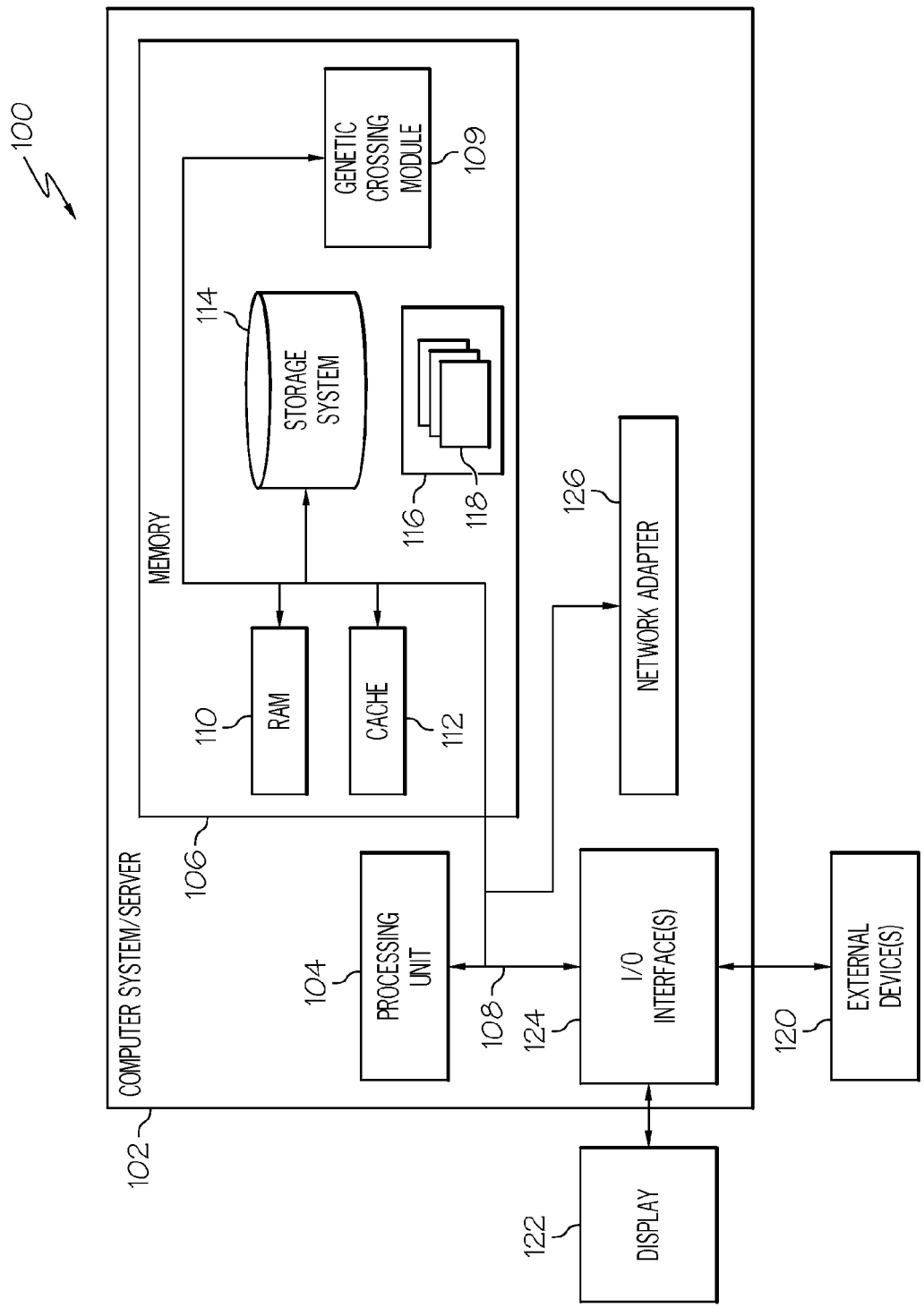
FIG. 1 is a block diagram illustrating one example of an operating environment according to one embodiment of the present invention.

FIG. 1 illustrates a general overview of one operating environment 100 lossless compression of the enumeration space of founder line crosses according to one embodiment of the present invention. In particular, FIG. 1 illustrates an information processing system 102 that can be utilized in embodiments of the present invention. The information processing system 102 shown in FIG. 1 is only one example of a suitable system and is not intended to limit the scope of use or functionality of embodiments of the present invention described above. The information processing system 102 of FIG. 1 is capable of implementing and/or performing any of the functionality set forth below. Any suitably configured processing system can be used as the information processing system 102 in embodiments of the present invention.

As illustrated in FIG. 1, the information processing system 102 is in the form of a general-purpose computing device. The components of the information processing system 102 can include, but are not limited to, one or more processors or processing units 104, a system memory 106, and a bus 108 that couples various system components including the system memory 106 to the processor 104.

The bus 108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 106, in one embodiment, comprises a genetic crossing module 109. It should be noted that even though FIG. 1 shows the genetic crossing module 109 residing in the main memory, the genetic crossing module 109 can reside within the processor 104, be a separate hardware component, and/or be distributed across a plurality of information processing systems and/or processors. The genetic crossing module 109, in one embodiment, is configured to provide a lossless compression of the enumeration spacer of founder line crosses. A founder line, in one embodiment, is a fixed composition of a species. A cross is the offspring resulting from breeding between two different individuals and carries a portion of the genetic material from both of the individuals.

In one embodiment, the crossing module 109 enumerates all possible variations that can be obtain by crossing N founders in at most G generations. The genetic crossing module 109 identifies and removes all duplicate computations and space redundancies. With respect to space redundancy, the genetic crossing module 109 identifies syntactically distinct, but semantically indistinct points, in the enumeration space. Stated differently, distinct components that result in indistinct statistical characteristics (semantically equivalent) are identified and removed.

The system memory 106 can also include computer system readable media in the form of volatile memory, such as random access memory (RAM) 110 and/or cache memory 112. The information processing system 102 can further include other removable/non-removable, volatile/non-volatile computer system storage media. By way of example only, a storage system 114 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. The memory 106 can include at least one program product having a set of program modules that are configured to carry out the functions of an embodiment of the present invention.

Program/utility 116, having a set of program modules 118, may be stored in memory 106 by way of example, and not limitation, as well as an operating system, one or more application programs, other program modules, and program data. Each of the operating system, one or more application programs, other program modules, and program data or some combination thereof, may include an implementation of a networking environment. Program modules 118 generally carry out the functions and/or methodologies of embodiments of the present invention.

The information processing system 102 can also communicate with one or more external devices 120 such as a keyboard, a pointing device, a display 122, etc.; one or more devices that enable a user to interact with the information processing system 102; and/or any devices (e.g., network card, modem, etc.) that enable computer system/server 102 to communicate with one or more other computing devices. Such communication can occur via I/O interfaces 124. Still yet, the information processing system 102 can communicate with one or more networks such as a local area network (LAN), a general wide area network (WAN), and/or a public network (e.g., the Internet) via network adapter 126. As depicted, the network adapter 126 communicates with the other components of information processing system 102 via the bus 108. Other hardware and/or software components can also be used in conjunction with the information processing system 102. Examples include, but are not limited to: microcode, device drivers, redundant processing units, external disk drive arrays, RAID systems, tape drives, and data archival storage systems.

Lossless Compression of the Enumeration Spacer of Founder Line Crosses

As will be discussed in greater detail below, the crossing module 109 takes as input a set of founder lines (F) and a maximum number of generations G. In one embodiment, the crossing module 109 also takes as input a limit for each founder line Z in F on the number of times, $n_Z$ Z can be used in a cross. Based on this input the crossing module 109 generates a set of genetic crossing templates of a height h. The crossing module 109 then removes any redundant genetic crossing templates resulting in an updated set of genetic crossing templates. A set of genetic crossing instances is then generated for each genetic crossing template in the updated set of genetic crossing templates based on the set of founder lines F. Any redundant instances are removed from each set of genetic crossing instances. The height h is the incremented by 1 and the above process is repeated until h=G. The crossing module 109 then outputs all possible crossing variations for the set of founder lines F with all redundancies having been removed.

The following is a general framework for one or more embodiments of the present invention. Let the N founder lines be written as A, B, C, ..., Z for convenience. In one embodiment, an "operator" cross is binary and defined on a pair of "operands". Therefore, an infix notation with nested parenthesis can be utilized and the cross is written as x. For example:

$$v_1 = ((A \times B) \times C) \text{ Or } v_2 = ((D \times E) \times (A \times C)).$$

The cross of $v_1$ and $v_2$ is composed as follows:

$$v_3 = v_1 \times v_2 = (((A \times B) \times C) \times ((D \times E) \times (A \times C))).$$

Also, backcrosses can be represented in this notation as well. For example backcrossing with A three times can be represented as:

$$v_4 = ((((A \times B) \times A) \times A) \times A).$$

In one embodiment, v (i.e., a set of crosses) can be represented as a binary tree. For example, FIG. 2 shows one example of a binary tree 202 representing $v_1$ and another example of a binary tree 204 representing $v_2$. A founder line, in one embodiment, is represented by a leaf (open node) of the binary tree. For example, in the first binary tree 202 founder lines A, B, and C are represented by leaf nodes 206, 208, 210, respectively. In the second binary tree 204 founder lines D, E, A, and C are represented by leaf nodes 212, 214, 216, 218, respectively. The founder labels (A, B, C, D, E) are the labels of the corresponding leaf nodes 206, 208, 210, 212, 214, 216, 218.

Each row/level of the tree corresponds to a cross (x) in v. The product (offspring) of each cross (x) in v is represented with an internal (closed) node within the tree 202, 204. For example, in the first binary tree 202 the product ($p_1$) of the cross between founder A 206 and found B 208 is represented with a first internal node 220. The product of the cross between $p_1$ 220 and founder C 210 is represented with a second internal node 222, which is the root node of the binary tree 202. In the second binary tree 202 the product ($p_1$) of the cross between founder A 206 and found B 208 is represented with a first internal node 220. The product ($p_2$) of the cross between $p_1$ 220 and founder C 210 is represented with an second internal node 222, which is the root node of the binary tree 202. In the second binary tree 204 the product ($p_3$) of the cross between founder D 212 and found E 214 is represented with a third internal node 224. The product ($p_4$) of the cross between founder D 212 and founder E 214 is represented with a fourth internal node 226. The product ($p_5$) of the cross between $p_3$ 224 and product $p_4$ 226 is represented with a fifth internal node 228, which is the root node of the binary tree 204.

In one embodiment, the crossing module 109 identifies all the common components between a set of binary trees so that these common components are enumerated (or computed) exactly once. In this embodiment, let $S_j$ denote all the binary trees with exactly j−1 internal nodes (or j−1 crosses), wherein $v_x$ is a given binary tree in $S_j$. Then, for a $v_1 \in S_{j_1}$ and $v_2 \in S_{j_2}$, $v_3$ can be constructed by introducing a new node (or cross) with the two descendants (i.e., the roots) of $v_1$ and $v_2$, as compared to re-creating the common elements of $v_1$ and $v_2$. Stated differently, the only difference between the binary tree for $v_3$ and the binary tree(s) for $v_1$ and $v_2$ is the cross between the roots of the tree(s) in $v_1$ and $v_2$. Therefore, the crossing module 109 can take the tree(s) previously computed for $v_1$ and $v_2$, and add a new node (or cross) based on the cross of the root nodes of $v_1$ and $v_2$ to obtain the tree for $v_3$. The crossing module 109 does not need to re-create the binary trees for $v_1$ and $v_2$.

Also $v_3$ has exactly $j_1+j_2+1$ internal nodes. This leads to the following general definition of $S_j$:

$$S_1 = F = \text{set of founder lines},$$

$$S_{(j>1)} = \bigcup_{i=1}^{\lfloor j/2 \rfloor} S_i \otimes S_{j-i},$$

where ⊗ is defined as:

$$S \otimes S' = \{v \times v' | (v \neq v'), v \in S, v' \in S'\}.$$

Therefore, to obtain/enumerate all possible binary tree S of a given height j the crossing module 109 performs all possible pairwise crosses of between trees (e.g., each v in $S_i$ and $S_{j-i}$) of a lesser height than j. The result of this operation is a set of unique binary trees.

The following is an example of enumerating all possible variations that can be obtained by crossing a set of founder lines F for 5 generations. In this example, the set of binary trees of height 1 ($S_1$) are enumerated as the crosses between the founder lines F. The crossing module 109 then takes the pairwise crosses between $S_1$ and itself to obtain $S_2$ such that $S_2 = S_1 \otimes S_1$. The pairwise crosses between $S_1$ and $S_2$ are then taken to obtain $S_3$ such that $S_3 = S_1 \otimes S_2$. The crossing module 109 then takes the union of the pairwise crosses between $S_1/S_3$ and $S_2/S_2$ to obtain $S_4$ such that $S_4 = (S_1 \otimes S_3) \cup (S_2 \otimes S_2)$. $S_5$ is then obtained by taking the union of the pairwise crosses between $S_1/S_4$ and $S_2/S_3$ to obtain $S_5$ such that $S_5 = (S_1 \otimes S_4) \cup (S_2 \otimes S_3)$.

As can be seen, the sum of the heights (e.g., 1 and 2) of two sets of trees being crossed equal the height (e.g., 3) of the set being obtained/enumerated. Also, when multiple leaf nodes with the same labels are allowed (backcrosses), then crossing module 109 keeps track of the multiplicity of the leaf labels. In addition, the size (or height) of the binary tree v can be bounded. For example, a binary tree v can be bounded either in terms of the maximum number of crosses allowed or in terms of maximum number of generations. Note that the number of generations is the height h of the binary tree. Thus, $S_j$ can still be used in these problem settings as well.

In many instances $v_1 \neq v_2$, i.e., they are syntactically distinct. However, $v_1$ and $v_2$ may represent the same statistically equivalent population. Stated differently, the binary trees $v_1$ and $v_2$ are distinct, but the resulting statistical populations comprise redundancies. Then, although $v_1 \neq v_2$, the two populations after fixation would have extremely similar, if not identical, statistical characteristics, i.e., they are semantically indistinct. Therefore, two semantically indistinct trees can be written as $v_1 \approx v_2$.

In one embodiment, the crossing module 109 captures semantic equivalence (semantic indistinctness) through a signature of. In this embodiment, let v be a cross configuration. Then the signature of v is:

$$\text{sig}(v) = \bigcup_Z Z_{0.5^{d_1} + 0.5^{d_2} + \ldots + 0.5^{d_K}},$$

where Z is a founder line in v, 0.5 is the expected genetic code contribution of Z with one cross, and $d_k$ is the distance of the kth instance (as a backcross) of Z from the root in the binary tree representation of v, k=1, 2, . . . K . For each v, the sum of the genetic contribution from all genetic lines will be equal to 1:

$$\sum_{Z_x \in sig(v)} x = 1.$$

Assuming the root of v is 1.0, each branch of the tree is divided by two successively to give the contribution of each leaf node to the root.

For example, consider the following crosses $v_1=((A \times B) \times C)$, $v_2=((D \times E) \times (A \times C))$, $v_3=((D \times C) \times (A \times E))$, and $v_4=((((A \times B) \times A) \times A) \times A)$, The crossing module 109 calculates the signature of $v_1$ as sig $(v_1)=A_{0.5}{}^2 B_{0.5}{}^2 C_{0.5}{}^1$, the signatures of $v_2$ and $v_3$ as sig $(v_2)=sig(v_3)=A_{0.5}{}^2 C_{0.5}{}^2 D_{0.5}{}^2 E_{0.5}{}^2$; and the signature of $v_4$ as $sig(v_4)=A_{0.5}{}^{4+0.5^3+0.5^2+0.5^1} B_{0.5}{}^4$. As can be seen, $v_2 \neq v_3$, but their signatures show that they are semantic equivalent.

Consider another example with the following crosses $v_5 = (E \times ((A \times D) \times ((E \times B) \times C)))$ and $v_6=(E \times (D \times (E \times B)) \times (C \times A))$. The binary trees 302, 304 for $v_5$ and $v_6$, respectively, are shown in FIG. 3. As can be seen, $v_5$ and $v_6$ provide different backcross configurations and syntactically distinct crosses. However, the signatures of $v_5$ and $v_6$ are semantically equivalent: sig $(v_5)$=sig $(v_6)=A_{0.5}{}^3 B_{0.5}{}^4 C_{0.5}{}^3 D_{0.5}{}^3 E_{0.5}{}^{1+0.5^4}$ When the crossing module 109 identifies semantically equivalent crosses, the manager 109 marks these crosses as semantically equivalent. The crossing module 109 can then notify a user of the semantically equivalent crosses and/or remove one of the semantically equivalent crosses in a set of semantically equivalent crosses when providing a list of enumerated crosses for a given set of founder lines to the user.

The following is a more detailed discussion on computing/identifying semantically indistinct crosses. Let h be the height of the binary tree representation of a given cross. A template u is a configuration with place holders for the leaves. When the leaves of u are assigned the founder lines, then v is an instance of u. Thus, u is a template that captures the crossing topology, which can be instantiated by assignment of founder lines to the leaf nodes (open nodes). If u is a cross, then L(u) is an array where each index corresponds to height h (i.e., the distance from the root) and the value corresponds to the number of leaf nodes in the binary tree representation of u. L(u) can be modified as follows:

If $u_3=u_1 \times u_2$ then $L(u_3)=L(u_1)+L(u_2)$ after aligning for the depths appropriately in the arrays.

FIGS. 4-8 show one example of enumerating semantically indistinct crosses utilizing templates u. It should be noted that the following examples utilizes the notation of $u_{mn}$ where u is a template, m is the height h of a tree (or the length of the vector)–1, and n is an index 1, . . . , M of the M possible templates. For example, when h=2, there are only two templates b and c.

Figure 4:
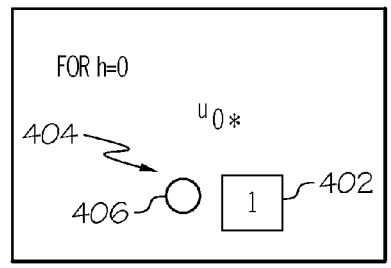
FIGS. 4-8 illustrate various examples of generating a set of genetic crossing templates for different heights according to one embodiment of the present invention.

In FIGS. 4-8, a set of vertically stacked boxes (referred to herein as "arrays") represent L(•). Each box (referred to herein as an "entry") of an array is an index, where the index progresses in descending order. For instance, for $u_{1a}$, the index goes from 1 down to 0 and for $u_{2b}$ the index goes from 2 down to 0. In the example of FIG. 4, the crossing module 109, configures a template $u_0$ for h=0 with a single entry array 402 comprising the value 1. That is, the binary tree representation 404 of template $u_0$ does not comprises any crosses (h=0). The index value of 1 within the array entry 402 indicates that there is one leaf node (hollow circle) in the binary tree representation 404 of $u_0$.

Figure 5:
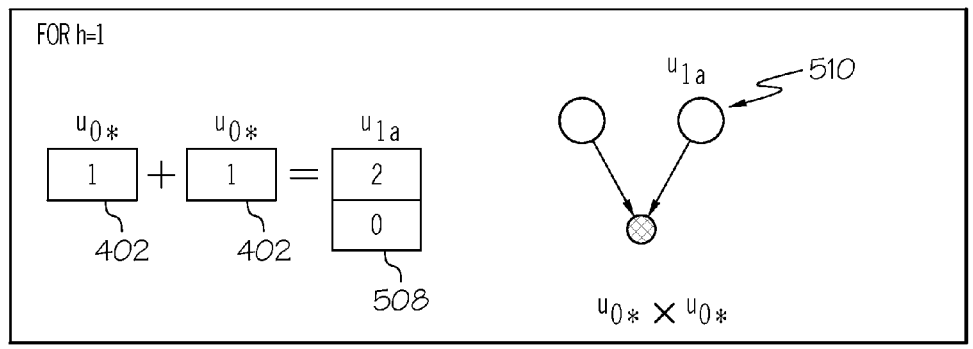

FIG. 5 shows that, for h=1, the crossing module 109 adds the single entry array 402 of $u_0$ with itself to obtain two-entry array 508 for $u_{1_a}$. This array 508 comprises a first entry comprising the value of 2 and a second entry comprising the value of 0. That is, the binary tree representation 510 of template $u_{1_a}$ comprises a cross between two leaf nodes at the top-most level L of the tree 510 resulting in a root internal node in the subsequent level L-1.

Figure 6:
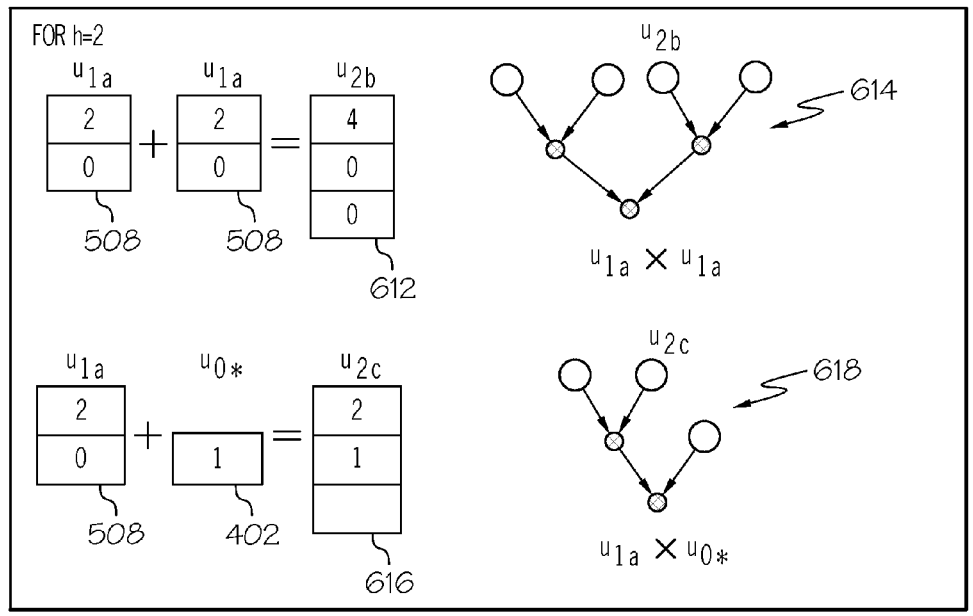

FIG. 6 shows that, for h=2, the crossing module 109 adds the entry array 508 of $u_{1_a}$ with itself to obtain a three-entry array 612 for $u_{2_b}$. This array 612 comprises a first entry comprising the value of 4, a second entry comprising the value of 0, and a third entry comprising the value of 0. That is, the binary tree representation 614 of $u_{2_b}$ comprises four leaf nodes in the top most-most level L. This binary tree 614 also comprises a first cross between two leaf nodes and a second cross between two leaf nodes in the top-most level L; a cross between two internal nodes in level L-1; and a root internal node in the bottom level L-2.

FIG. 6 further shows that the crossing module 109 also adds the array 508 of $u_{1_a}$ with the array 402 of $u_0$ to obtain a three-entry array 616 for $u_{2_c}$. This array 616 comprises a first entry comprising the value of 2, a second entry comprising the value of 1, and a third entry comprising the value of 0. That is, the binary tree representation 618 of $u_{2_c}$ comprises a two leaf nodes in the top-most level L and one leaf node in the level L-1. The binary tree 618 further comprises a cross between two leaf nodes in the top-most level L; a cross between an internal node and a leaf node in level L-1; and a root internal node in the bottom level L-2.

Figure 7:
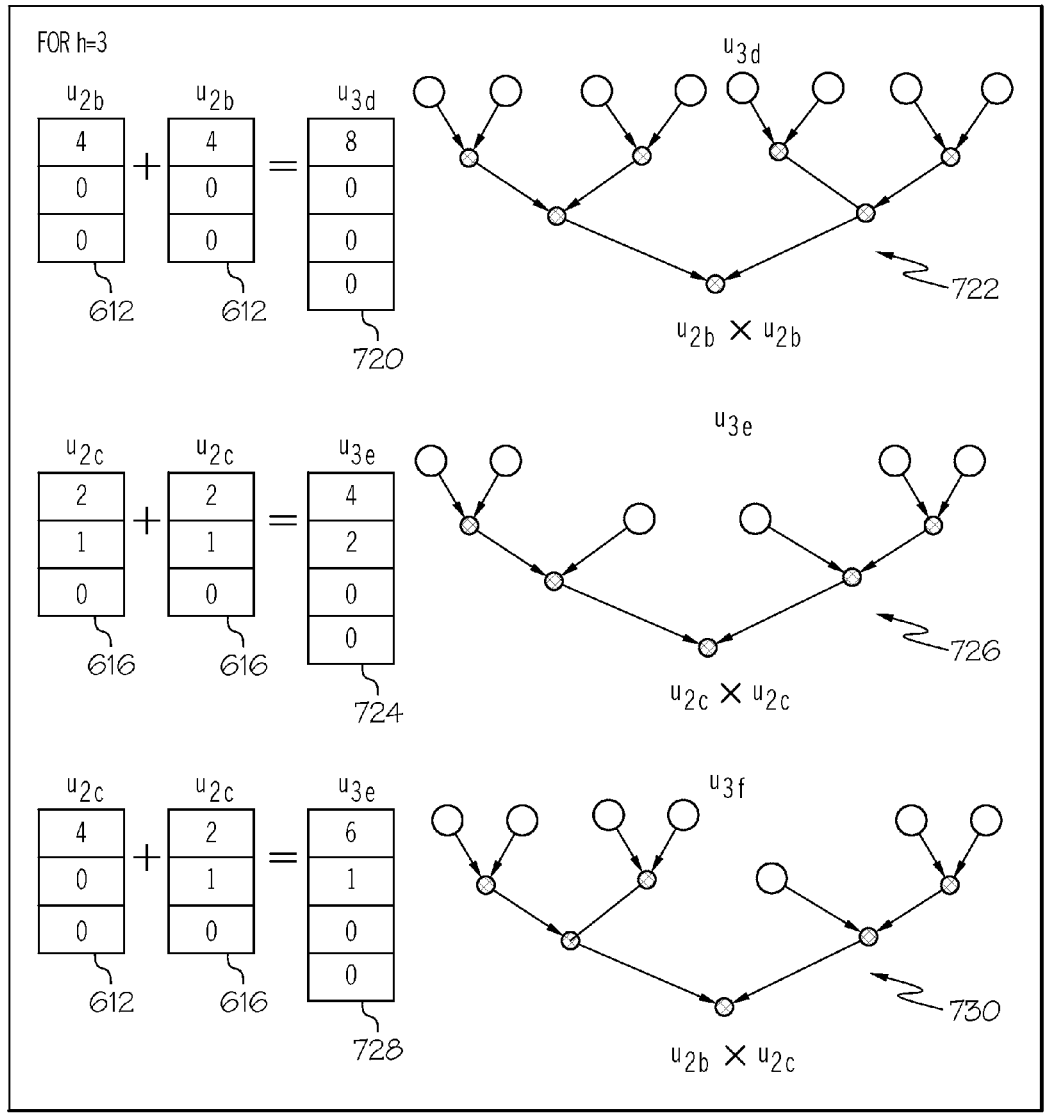

FIG. 7 that the crossing module 109, for h=3, adds the array 612 of $u_{2_b}$ with itself to obtain a four entry array 720 for $u_{3_d}$. This array 720 comprises a first entry comprising the value of 8, a second entry comprising the value of 0, third entry comprising the value of 0, and a fourth entry comprising the value 0. That is, the binary tree representation 722 of $u_{3_d}$ comprises eight leaf nodes in the top-most level L. The binary tree 722 further comprises a first cross between a first set of leaf nodes, a second cross between a second set of leaf nodes, a third cross between a third set of leaf nodes, and a fourth cross between a fourth set of leaf nodes in the top-most level L; a first cross between a first set of internal nodes and a second cross between a second set of internal nodes in level L-1; a cross between a set of internal nodes in level L-2; and a root internal node in level L-3.

FIG. 7 further shows that the crossing module 109 adds the array 616 of $u_{2_c}$ with itself to obtain a four entry array 724 for $u_{3_e}$. This array 724 comprises a first entry comprising the value of 4, a second entry comprising the value of 2, third entry comprising the value of 0, and a fourth entry comprising the value 0. That is, the binary tree representation 726 of $u_{3_e}$ comprises four leaf nodes in the top-most level L and two leaf nodes in level L-1. The binary tree 726 further comprises a first cross between a first set of leaf nodes and a second cross between a second set of leaf nodes in the top-most level L; a first cross between a first internal node and a first leaf node and a second cross between a second internal node and a second leaf node in level L-1; a cross between a set of internal nodes in level L-2; a root internal node in level L-3.

The crossing module 109 also adds the array 612 of $u_{2_b}$ with the array 616 of $u_{2_c}$ to obtain a four entry array 728 for $u_{3_f}$. This array 728 comprises a first entry comprising the value of 6, a second entry comprising the value of 1, third entry comprising the value of 0, and a fourth entry comprising the value 0.

That is, the binary tree representation 730 of $u_{3_f}$ comprises six leaf nodes within the top-most level L and one leaf node in level L-1. The binary tree 730 further comprises a first cross between a first set of leaf nodes, a second cross between a second set of leaf nodes, and a third cross between a third set of leaf nodes in the in the top-most level L; a first cross between a set of internal nodes and a second cross between a leaf node and an internal node in level L-1; a cross between a set of internal nodes in level L-2; a root internal node in level L-3.

Figure 8:
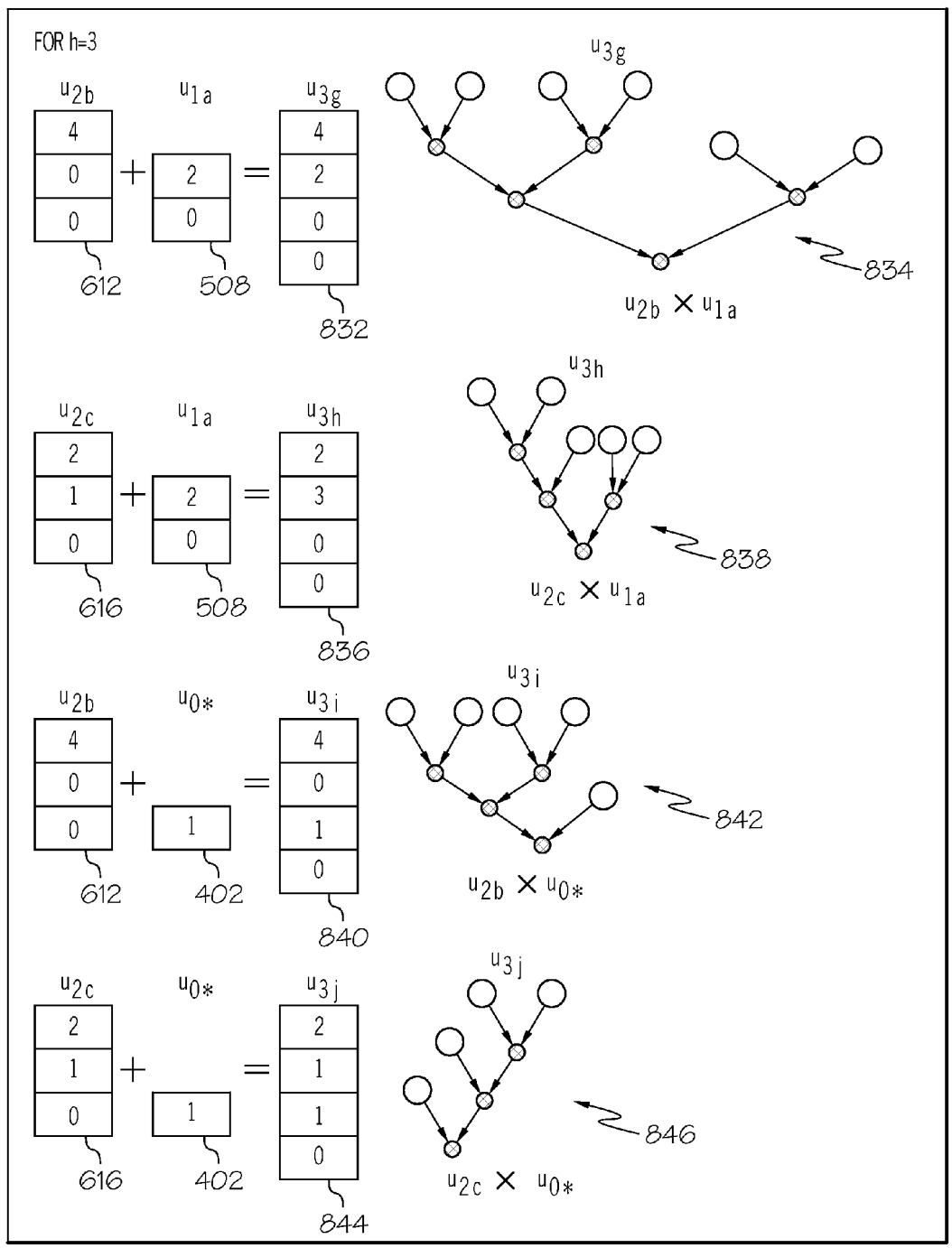

Continuing with h=3, FIG. 8 further shows that the crossing module 109 adds the array 612 of $u_{2_b}$ with the array 508 of $u_{1_a}$ to obtain a four entry array 832 for $u_{3_g}$. This array 832 comprises a first entry comprising the value of 0, a second entry comprising the value of 0, and third entry comprising the value of 2, and a fourth entry comprising the value 4. That is, the binary tree representation 834 of $u_{3_g}$ comprises four leaf nodes in the top-most level L and two leaf nodes in level L-1. The binary tree 834 further comprises a first cross between a first set of leaf nodes and a second cross between a second set of leaf nodes in the in the top-most level L; a first cross between a set of internal nodes and a second cross between a set of leaf nodes in level L-1; a cross between a set of internal nodes in level L-2; and a root internal node in level L-3.

The crossing module 109 further adds the array 616 of $u_{2_e}$ with the array 508 of $u_{1_a}$ to obtain a four-entry array 836 for $u_{3_h}$. This array 836 comprises a first entry comprising the value of 0, a second entry comprising the value of 0, and third entry comprising the value of 3, and a fourth entry comprising the value 2. That is, the binary tree representation 838 of tt, comprises two leaf nodes in the top-most level L and three leaf nodes in level L-1. The binary tree 836 further comprises a cross between two leaf nodes in the in the top-most level L; a first cross between a first internal node and a first leaf node, and second cross between two leaf nodes in level L-1; a cross between a set of internal nodes in level L-2; and a root internal node in level L-3.

FIG. 8 further shows that the crossing module 109 adds the array 612 of $u_{2_b}$ with the array 402 of $u_{0}$ to obtain a four-entry array 840 for $u_{3_i}$. This array 840 comprises a first entry comprising the value of 0, a second entry comprising the value of 1, and third entry comprising the value of 0, and a fourth entry comprising the value 4. That is, the binary tree representation 842 of $u_{3_i}$ comprises four leaf nodes in the top-most level L and 1 leaf node in level L-2. The binary tree 840 further comprises a first cross between a first set of leaf nodes and a second cross between a second set of leaf nodes in the top-most level L; a cross between two internal nodes in level L-1; a cross between an interval node and a leaf node in level L-2; and a root internal node in level L-3.

The crossing module 109 further adds the array 616 of $u_{2_e}$ with the array 402 of $u_{0}$ to obtain a four-entry array 844 for $u_{3_j}$. This array 844 comprises a first entry comprising the value of 0, a second entry comprising the value of 1, and third entry comprising the value of 1, and a fourth entry comprising the value 2. That is, the binary tree representation 846 of $u_{3_j}$ comprises two leaf nodes in the top-most level L, one leaf node in level L-1, and one leaf node in level L-2. The binary tree 846 further comprises a cross between two leaf nodes in the top-most level L; a cross between a leaf node and an internal node in level L-1; a cross between a leaf node and an internal node in level L-2; and a root internal node in level L-3.

The crossing module 109 identifies semantically equivalent crosses using templates as follows. Let $u_1$ and $u_2$ be two templates with $L(u_1)=L(u_2)$. Then for each instance $v_1$ of $u_1$ there exists an instance $v_2$ of $u_2$ such that sig $(v_1)$=sig $(v_2)$. For example, in the example shown in FIGS. 4-8 the crossing module 109 determines $L(u_{3_e})=L(u_{3_g})u_{3_e} \approx u_{3_g}$, i.e., each entry in the array 724 for $u_{3_e}$ comprises a matching value in a corresponding entry of the array for $u_{3_g}$. Therefore, the crossing module 109 identifies $u_{3_e}$ and $u_{3_g}$ as being semantically equivalent (redundant) and removes one of $u_{3_e}$ and $u_{3_g}$ from the set of genetic crossing templates. This results in an updated set of genetic crossing templates with redundancies between templates having been removed.

The crossing module 109 the generates a set of genetic crossing instances for each genetic crossing template in the updated set of genetic crossing templates based on the set of founder lines. For example, consider the genetic crossing template 612 for $u_{2_b}$ shown in FIG. 6 and the following set of founder lines A, B, and C. The crossing module 109 labels each of the leaf nodes in the template 612 with one of the founder lines. For example, the first leaf node can be labeled A, the second leaf node can be labeled B, the third leaf node can be labeled C, and the fourth leaf node can be labeled A. This combination of founder line labeling is considered one instance of the genetic crossing template 612 for $u_{2_b}$. Another instance could have the first leaf node labeled A, the second leaf node labeled C, the third leaf node can be labeled B, and the fourth leaf node can be labeled A The crossing module 109 creates a separate instance of this genetic crossing template 612 for each possible combination/variation of founder line assignment for the leaf nodes of the template 612.

In one embodiment, the set of genetic crossing instances for a given template $u_{hx}$ is generated by crossing all previously generated instances of templates with a height less than h with each other. Once the crossing module 109 generates (or during the generation process) the genetic cross instances of the set of templates any redundant instances are removed. Redundant instances comprise the same signature. For example, if $v_5$ and $v_6$ discussed above are instances of the same genetic crossing template the crossing module 109 identifies these two instances as redundant since sig $(v_5)$=sig $(v_6)=A_{0.5}{}^3B_{0.5}{}^4C_{0.5}{}^3D_{0.5}{}^3E_{0.5}{}^1{}_{+0.5}{}^4$. Therefore one of these two signatures is removed from the set of instances for the genetic crossing template resulting in an updated set of instances. The crossing module 109 can then provide a user with a list of enumerated crosses (i.e., all sets of genetic crossing instances) for the given set of founder lines with all redundancies having been removed.

Figure 9:
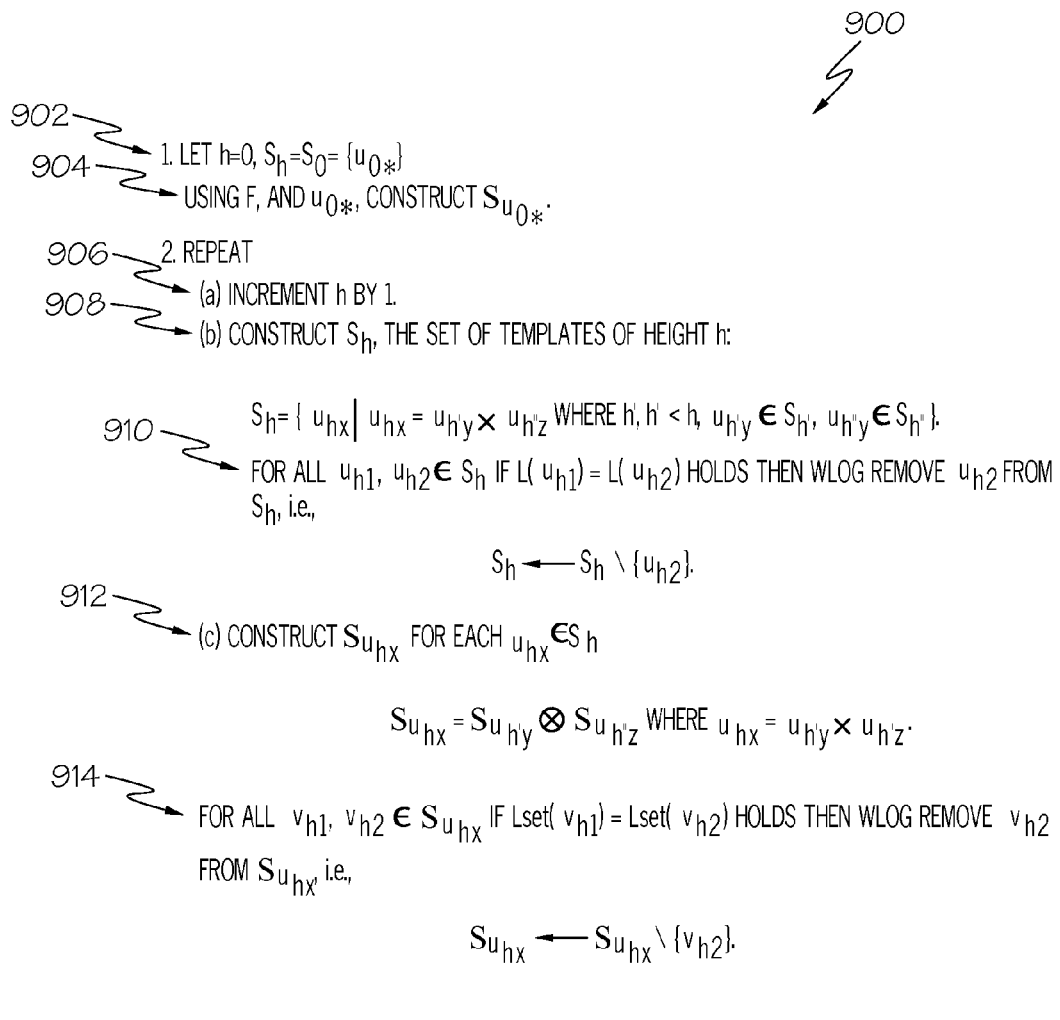
FIG. 9 illustrates one example of an algorithm for lossless compression of the enumeration space for found line crosses according to one embodiment of the present invention.

FIG. 9 shows one example of algorithm 900 for the operations performed by the crossing module 109 discussed above. In particular, the algorithm 900 of FIG. 9 illustrates a process for the enumerating the space of founder line crosses according to the following conditions: 1.) only semantically distinct configurations are outputted and 2.) all intermediate computations are performed exactly one time (i.e., no component of each v is computed more than once). For example, two semantically distinct crossings (binary trees with founder lines in the leafs) X and Y may each contain a single sub-tree Z. However, in one embodiment, the crossing module 109 only needs to determine the crossing of sub-tree Z once. That is, the crossing module 109 does not need to compute the crossings involved in X and Y separately. Instead, because the crossing module 109 has already computed the crossings in Z the crossing module 109 uses this previous computation to compute the crossings of X and Y.

In of FIG. 9, u is a template. Therefore, $S_u$={v|v is an instance of template u}. Also, if v is a cross configuration, then Lset(v) is an array of sets of founder lines where each index corresponds to height h, the distance from the root, and the value corresponds to the founder line assignments to the leaf nodes in the binary tree representation of v. Also, two instance sets $S_{u_1}$ and $S_{u_2}$ are equivalent, written as $S_{u_1} \cong S_{u_2}$ if and only if the following holds: for each $v_1 \in S_{u_1}$, there exists $v_2 \in S_{u_2}$ such that $\text{Lset}(v_1)=\text{Lset}(v_2)$ and vice-versa. Let $v_i$ be an instance of template $u_i$, $i=1,2$. Then $L(u_1)=L(u_2) \Leftrightarrow S_{u_1} \cong S_{u_2}$. Let $v_1$ and $v_2$ be two distinct instances of template u. Then $\text{Lset}(v_1)=\text{Lset}(v_2) \Rightarrow v_1 \approx v_2$. Also, if $u_{hx}$ is a template of height h then $v_{hx}$ is a cross configuration of height h.

The crossing module 109 takes as input the founder line set F; for each $Z \in F$, $n_Z$, the number of times Z can be used in a cross configuration; and the maximum number of generations G. Based on this input and the operations described in the algorithm 900 of FIG. 9, the crossing module 109 outputs all possible crosses, with no repetition in intermediate computations or semantically equivalent crosses. All configurations of height (number of generations) h are captured in the sets of the form $S_{u_{hx}}$.

The crossing module 109 performs each of the operations shown in FIG. 9 in an iterative fashion. Also, if h=1, no founder line is used more than once. This avoids crossing a founder line with itself. If h>1, no founder line Z is used more than $n_Z$ times in v. That is, if founder line Z is used more than $n_Z$ times in instance v, then v is removed from $S_{u_{hx}}$. In line 902 of the algorithm 900 the crossing module 109 initializes the current height h=0, and the current templates of height h, $S_h = S_0 = \{u_{0*}\}$. The crossing module 109 then constructs the current set of instances of $u_{0*}$, $S_{u_{0*}}$, by filling in templates $u_{0*}$ using founder lines F, as shown in line 904. In line 906 the crossing module 109 increments the current height h by 1. In line 908 the crossing module 109 then constructs $S_h$, which is the template set of height h:

$$S_h = \{u_{hx} | u_{hx} = u_{h'y} \times u_{h''z} \text{ where } h', h'' < h, u_{h'y} \in S_{h'}, u_{h''z} \in S_{h''}\}.$$

For example, the crossing module 109 takes a template $u_{h'y}$ of height h'<h and another template $u_{h''z}$ of height h''<h and crosses $(u_{h'y} \times u_{h''z})$ the two templates in order to get a new template $u_{hx}$. In line 910, for all $u_{h1}, u_{h2} \in S_h$ if $L(u_{h1})=L(u_{h2})$ holds then WLOG the crossing module 109 removes $u_{h2}$ from $S_h$, i.e., $S_h \leftarrow S_h \setminus \{u_{h2}\}$. That is, the crossing module 109 prunes the set $S_h$ by removing all redundant templates $u_{h1}$, where redundant indicates there exists another template $u_{h2}$ in $S_h$ such that for the binary trees given by the templates $u_{h1}$ and $u_{h2}$ the number of open leafs where founder lines can be inserted at each height are equal, i.e. $L(u_{h1})=L(u_{h2})$.

In line 912, the crossing module 109 constructs the set of instances $S_{u_{hx}}$ of template $u_{hx}$ for each template $u_{hx}$ in the set of templates $S_h$ of height h, $$S_{u_{hx}} S_{u_{h'y}} \otimes S_{u_{h''z}} \text{ where } u_{hx} = u_{h'y} \times u_{h''z}.$$

That is, the crossing module 109 takes all instances $S_{u_{h'y}}$ of template $u_{h'y}$ and crosses them with all instances $S_{u_{h''z}}$ of template $u_{h''z}$ in order to construct all instances $S_{u_{hx}}$ of template $u_{hx}$ where template $u_{hx}$ is a cross of templates $u_{h'y}$ and $u_{h''z}$.

In line 914, for all $v_{h1}, v_{h2} \in S_{u_{hx}}$ if $\text{Lset}(v_{h1})=\text{Lset}(v_{h2})$ holds then WLOG the crossing module 109 removes $v_{h2}$ from $S_{u_{hx}}$, i.e., $S_{u_{hx}} \leftarrow S_{u_{hx}} \setminus \{v_{h2}\}$. That is, the crossing module 109 prunes the set $S_{u_{hx}}$ by removing all redundant instances $v_{h1}$, where redundant indicates there exists another instance $v_{h1}$ in $S_{u_{hx}}$ such that the two leaf sets of $v_{h1}$ and $v_{h2}$ are equal, i.e. $\text{Lset}(v_{h1})=\text{Lset}(v_{h2})$. The crossing module 109 the repeats lines 906 to 914 until h=G and outputs an enumeration of all possible crosses, with no repetition in intermediate computations or semantically equivalent crosses. All configurations of height (number of generations) h are captured in the sets of the form $S_{u_{hx}}$.

Operational Flow Diagrams

Figure 10:
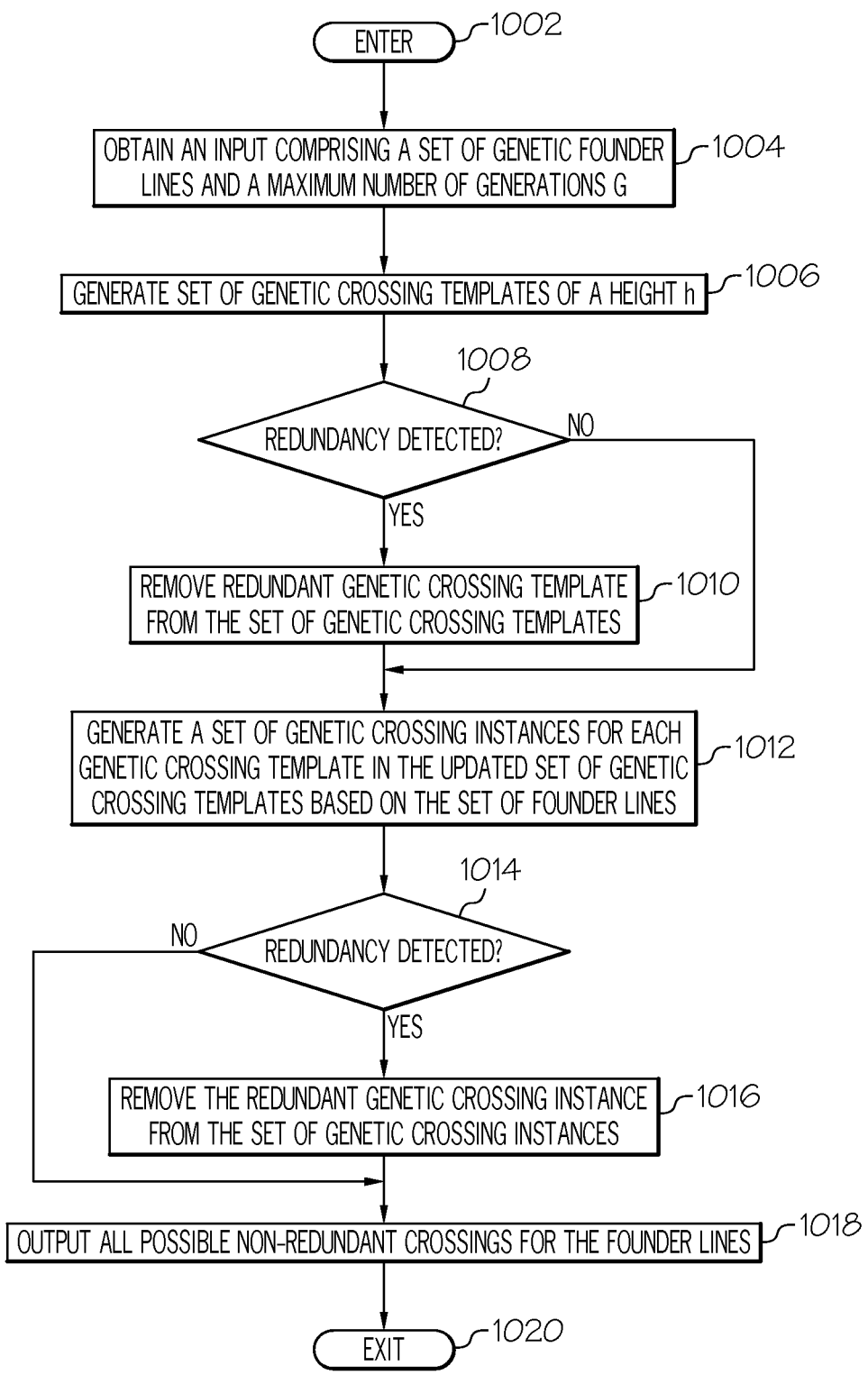
FIG. 10 is an operational flow diagram illustrating one example of a process for lossless compression of the enumeration space for found line crosses according to one embodiment of the present invention.

FIG. 10 is an operational flow diagram illustrating one example of an overall process for lossless compression of the enumeration space of found lines. The operational flow diagram begins at step 1000 and flows directly to step 1004. The genetic crossing module 109, at step 1004, obtains an input comprising a set of genetic founder lines and a maximum number of generations G. The genetic crossing module 109, at step 1006, generates generating a set of genetic crossing templates of a height h. Each the set of genetic crossing templates represents a binary tree. The binary tree comprises h levels representing a given generation. Each of the h levels comprising a set of nodes wherein when h>0 one or more of the h levels of the binary tree correspond to at least one cross between at least one pair of nodes in the set of nodes. Each of the set of genetic crossing templates comprises an array of h entries. A position of an entry within the array corresponds to a level in the binary tree represented by the genetic crossing template. Each of the h entries in the array comprises a value indicating a number of leaf nodes in the set of nodes for the level in the binary tree.

The genetic crossing module 109, at step 1008, determines if at least a first genetic crossing template in the set of genetic crossing templates is redundant with respect to a second genetic crossing template in the set of genetic crossing templates. If the result of this determination is negative, the control flows to step 1012. If the result of this determination is positive, the genetic crossing module 109, at step 1010, removes the redundant genetic crossing template (e.g., the first genetic crossing template) from the set of genetic crossing templates. This process of removing the at least first genetic crossing template from the set of genetic crossing templates the redundant creates an updated set of genetic crossing templates.

The genetic crossing module 109, at step 1012, generates a set of genetic crossing instances for each genetic crossing template in the updated set of genetic crossing templates based on the set of founder lines. Each genetic crossing instance in the set of genetic crossing instances is the binary tree represented by the genetic crossing template in the updated set of genetic crossing templates with leaf nodes at each of the h levels labeled with one of the set of genetic founder lines. The set of genetic crossing instances comprises a genetic crossing instance for each of a plurality of different leaf node labeling variations based on the set of genetic founder lines.

The genetic crossing module 109, at step 1014 determines if at least a first genetic crossing instance in the set of genetic crossing instances is redundant with respect to a second genetic crossing instance in the set of genetic crossing instances. If the result of this determination is negative, the control flows to step 1018. If the result of this determination is positive, the genetic crossing module 109, at step 1016, removes the redundant genetic crossing instance (e.g., the first genetic crossing instance) from the set of genetic crossing instances. This process of removing the at least first genetic crossing instance from the set of genetic crossing instances creates an updated set of genetic crossing instances. The genetic crossing module 109 repeats steps 1006 to 1016 until h=G. The genetic crossing module 109, at step 1018, then outputs all possible non-redundant crossing for the fonder lines. The control flow exits at step 1020.

Non-Limiting Examples

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems), and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer implemented method for providing lossless compression of an enumeration space for genetic founder lines, the computer implemented method comprising
obtaining an input comprising a set of genetic founder lines and a maximum number of generations G, wherein the following is iteratively performed for $h=0, 1, \ldots, G$:
generating a set of genetic crossing templates of a height h, wherein each of the set of genetic crossing templates represents a binary tree, the binary tree comprising h levels representing a given generation, each of the h levels comprising a set of nodes wherein when $h>0$ one or more of the h levels of the binary tree correspond to at least one cross between at least one pair of nodes in the set of nodes,
wherein each of the set of genetic crossing templates comprises an array of h entries, wherein a position of an entry within the array corresponds to a level in the binary tree represented by the genetic crossing template, each of the h entries in the array comprising a value indicating a number of leaf nodes in the set of nodes for the level in the binary tree; and determining if at least a first genetic crossing template in the set of genetic crossing templates is redundant with respect to a second genetic crossing template in the set of genetic crossing templates; and based on the at least first genetic crossing template being redundant, removing the at least first genetic crossing template from the set of genetic crossing templates, the removing creating an updated set of genetic crossing templates.

2. The computer implemented method of claim 1, wherein the determining comprises:

comparing the array of the at least first genetic crossing template with the array of the second genetic crossing template;

determining, based on the comparing, if the value within each entry of the array for the at least first genetic crossing template matches the value within each corresponding entry of the array for the second genetic crossing template; and determining that the at least first genetic crossing template is redundant with respect to the second genetic crossing template based on the value within each entry of the array for the at least first genetic crossing template matching the value within each corresponding entry of the array for the second genetic crossing template.

3. The computer implemented method of claim 1, wherein at least one of the set of genetic crossing templates of height h is generated by combining a previously generated genetic crossing template of a height less than h with another previously generated genetic crossing template of a height less than h.

4. The computer implemented method of claim 1, further comprising:

generating a set of genetic crossing instances for each genetic crossing template in the updated set of genetic crossing templates based on the set of founder lines, wherein each genetic crossing instance in the set of genetic crossing instances is the binary tree represented by the genetic crossing template in the updated set of genetic crossing templates with leaf nodes at each of the h levels labeled with one of the set of genetic founder lines, wherein the set of genetic crossing instances comprises a genetic crossing instance for each of a plurality of different leaf node labeling variations based on the set of genetic founder lines.

5. The computer implemented method of claim 4, further comprising:

determining if at least a first genetic crossing instance in the set of genetic crossing instances is redundant with respect to a second genetic crossing instance in the set of genetic crossing instances; and based on the at least first genetic crossing instance being redundant, removing the at least first genetic crossing instance from the set of genetic crossing instances, the removing creating an updated set of genetic crossing instances.

6. The computer implemented method of claim 5, wherein the determining comprises:

comparing the binary tree of the at least a first genetic crossing instance with the binary tree of the second genetic crossing instance;

determining, based on the comparing, if the label of each leaf node in the binary tree of the at least first genetic crossing instance matches a label of a corresponding leaf node in the binary tree of the second genetic crossing instance; and determining that the at least first genetic crossing instance is redundant with respect to the second genetic crossing instance based on the label of each leaf node in the binary tree of the at least first genetic crossing instance matching a label of a corresponding leaf node in the binary tree of the second genetic crossing instance.

7. The computer implemented method of claim 4, wherein at least one of the set of genetic crossing instances is generated by combining each of a previously generated set of crossing instances of a given genetic crossing template in the update set of genetic crossing templates with each of a previously generated set of crossing instances of at least one other genetic crossing template in the update set of genetic crossing templates.

* * * * *